United States Patent
Thompson et al.

(10) Patent No.: US 10,537,281 B2
(45) Date of Patent: *Jan. 21, 2020

(54) DECONGESTIVE THERAPY TITRATION FOR HEART FAILURE PATIENTS USING IMPLANTABLE SENSOR

(71) Applicant: Cardiac Pacemakers, Inc., St. Paul, MN (US)

(72) Inventors: Julie A. Thompson, Circle Pines, MN (US); Yousufali H. Dalal, Northbridge, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 144 days.

This patent is subject to a terminal disclaimer.

(21) Appl. No.: 15/446,794

(22) Filed: Mar. 1, 2017

(65) Prior Publication Data

US 2017/0172496 A1   Jun. 22, 2017

Related U.S. Application Data

(60) Continuation of application No. 13/620,462, filed on Sep. 14, 2012, now Pat. No. 9,655,520, which is a
(Continued)

(51) Int. Cl.
*A61B 5/0205* (2006.01)
*A61B 5/00* (2006.01)
(Continued)

(52) U.S. Cl.
CPC .......... *A61B 5/4839* (2013.01); *A61B 5/0031* (2013.01); *A61B 5/021* (2013.01);
(Continued)

(58) Field of Classification Search
CPC ............ A61N 1/36117; A61N 1/36521; A61N 1/3627; A61N 1/37258; A61N 1/36114;
(Continued)

(56) References Cited

U.S. PATENT DOCUMENTS

| 4,562,841 A | 1/1986 | Brockway et al. |
| 4,928,688 A | 5/1990 | Mower |

(Continued)

FOREIGN PATENT DOCUMENTS

| WO | WO-9718856 A1 | 5/1997 |
| WO | WO-0151123 A1 | 7/2001 |

(Continued)

OTHER PUBLICATIONS

"U.S. Appl. No. 13/620,462, Advisory Action dated Feb. 18, 2016", 10 pgs.

(Continued)

*Primary Examiner* — Christopher Koharski
*Assistant Examiner* — Pamela M. Bays
(74) *Attorney, Agent, or Firm* — Schwegman Lundberg & Woessner, P.A.

(57) ABSTRACT

Assessing decongestive therapy delivered to a heart failure patient involves use of an implantable sensor configured to sense a physiologic parameter indicative of the patient's diuresis status and a processor coupled to the implantable sensor. The sensor may comprise a thoracic fluid sensor, a heart sounds sensor, a cardiac chamber or arterial pressure sensor, a respiration sensor, or a blood chemistry sensor, for example. The processor is configured to determine if a target level of patient diuresis has been achieved based on a relationship between the sensed physiologic parameter and a threshold developed for the patient, and to produce an output in response to determining that the target level of patient diuresis has been achieved. The processor may be disposed in an implantable housing, in a patient-external housing, or in a network server system.

20 Claims, 7 Drawing Sheets

Related U.S. Application Data division of application No. 11/805,311, filed on May 23, 2007, now Pat. No. 8,271,080.

(51) Int. Cl.

| | | |
|---|---|---|
| *A61N 1/36* | (2006.01) | |
| *A61B 5/053* | (2006.01) | |
| *A61B 5/021* | (2006.01) | |
| *A61B 5/145* | (2006.01) | |
| *A61N 1/365* | (2006.01) | |
| *A61N 1/372* | (2006.01) | |
| *A61M 5/142* | (2006.01) | |
| *A61M 5/172* | (2006.01) | |
| *A61N 1/362* | (2006.01) | |
| *G06F 19/00* | (2018.01) | |
| *A61B 5/0402* | (2006.01) | |
| *A61B 7/04* | (2006.01) | |

(52) U.S. Cl.
CPC ........ *A61B 5/02055* (2013.01); *A61B 5/0537* (2013.01); *A61B 5/145* (2013.01); *A61B 5/14539* (2013.01); *A61B 5/14546* (2013.01); *A61B 5/4261* (2013.01); *A61B 5/4833* (2013.01); *A61M 5/14276* (2013.01); *A61M 5/1723* (2013.01); *A61N 1/365* (2013.01); *A61N 1/3627* (2013.01); *A61N 1/36114* (2013.01); *A61N 1/36135* (2013.01); *A61N 1/37258* (2013.01); *G06F 19/3456* (2013.01); *G06F 19/3481* (2013.01); *A61B 5/0402* (2013.01); *A61B 7/04* (2013.01); *A61M 2205/054* (2013.01); *A61M 2210/125* (2013.01); *G06F 19/3418* (2013.01)

(58) Field of Classification Search
CPC .............. A61M 5/1723; G06F 19/3418; G06F 19/3481; A61B 5/0031; A61B 5/021; A61B 5/4261; A61B 5/4833; A61B 5/4839; A61B 5/0537; A61B 5/145
See application file for complete search history.

(56) References Cited

U.S. PATENT DOCUMENTS

| | | | |
|---|---|---|---|
| 5,036,849 | A | 8/1991 | Hauck et al. |
| 5,133,353 | A | 7/1992 | Hauser |
| 5,179,945 | A | 1/1993 | Van Hofwegen et al. |
| 5,203,348 | A | 4/1993 | Dahl et al. |
| 5,230,337 | A | 7/1993 | Dahl et al. |
| 5,284,136 | A | 2/1994 | Hauck et al. |
| 5,313,953 | A | 5/1994 | Yomtov et al. |
| 5,314,459 | A | 5/1994 | Swanson et al. |
| 5,318,597 | A | 6/1994 | Hauck et al. |
| 5,334,222 | A | 8/1994 | Salo et al. |
| 5,360,442 | A | 11/1994 | Dahl et al. |
| 5,366,496 | A | 11/1994 | Dahl et al. |
| 5,376,106 | A | 12/1994 | Stahmann et al. |
| 5,388,578 | A | 2/1995 | Yomtov et al. |
| 5,391,200 | A | 2/1995 | KenKnight et al. |
| 5,397,342 | A | 3/1995 | Heil, Jr. et al. |
| 5,411,031 | A | 5/1995 | Yomtov |
| 5,540,727 | A | 7/1996 | Tockman et al. |
| 5,545,202 | A | 8/1996 | Dahl et al. |
| 5,603,732 | A | 2/1997 | Dahl et al. |
| 5,620,466 | A | 4/1997 | Haefner et al. |
| 5,662,688 | A | 9/1997 | Haefner et al. |
| 5,836,987 | A | 11/1998 | Baumann et al. |
| 5,882,352 | A | 3/1999 | Duncan et al. |
| 5,916,243 | A | 6/1999 | KenKnight et al. |
| 6,026,320 | A | 2/2000 | Carlson et al. |
| 6,044,298 | A | 3/2000 | Salo et al. |
| 6,055,454 | A | 4/2000 | Heemels |
| 6,221,011 | B1 | 4/2001 | Bardy |
| 6,270,457 | B1 | 8/2001 | Bardy |
| 6,277,072 | B1 | 8/2001 | Bardy |
| 6,280,380 | B1 | 8/2001 | Bardy |
| 6,285,907 | B1 | 9/2001 | Kramer et al. |
| 6,312,378 | B1 | 11/2001 | Bardy |
| 6,336,903 | B1 | 1/2002 | Bardy |
| 6,358,203 | B2 | 3/2002 | Bardy |
| 6,360,127 | B1 | 3/2002 | Ding et al. |
| 6,368,284 | B1 | 4/2002 | Bardy |
| 6,371,922 | B1 | 4/2002 | Baumann et al. |
| 6,398,728 | B1 | 6/2002 | Bardy |
| 6,411,848 | B2 | 6/2002 | Kramer et al. |
| 6,424,865 | B1 | 7/2002 | Ding |
| 6,440,066 | B1 | 8/2002 | Bardy |
| 6,459,929 | B1 | 10/2002 | Hopper et al. |
| 6,473,640 | B1 | 10/2002 | Erlebacher |
| 6,542,775 | B2 | 4/2003 | Ding et al. |
| 6,597,951 | B2 | 7/2003 | Kramer et al. |
| 6,666,826 | B2 | 12/2003 | Salo et al. |
| 6,892,095 | B2 | 5/2005 | Salo |
| 6,908,437 | B2 | 6/2005 | Bardy |
| 6,931,272 | B2 | 8/2005 | Burnes |
| 6,993,389 | B2 | 1/2006 | Ding et al. |
| 7,076,298 | B2 | 7/2006 | Padmanabhan et al. |
| 7,142,911 | B2 | 11/2006 | Boileau et al. |
| 8,271,080 | B2 | 9/2012 | Thompson et al. |
| 9,655,520 | B2 | 5/2017 | Thompson et al. |
| 2003/0130702 | A1 | 7/2003 | Kramer et al. |
| 2003/0216792 | A1* | 11/2003 | Levin ................ A61M 5/14276 607/48 |
| 2004/0077995 | A1 | 4/2004 | Ferek-Petric et al. |
| 2004/0167410 | A1 | 8/2004 | Hettrick |
| 2004/0172080 | A1* | 9/2004 | Stadler ................ A61B 5/0537 607/17 |
| 2004/0176813 | A1 | 9/2004 | Gelfand et al. |
| 2004/0199210 | A1 | 10/2004 | Shelchuk |
| 2004/0225332 | A1 | 11/2004 | Gebhardt et al. |
| 2004/0230230 | A1 | 11/2004 | Lindstrom et al. |
| 2004/0230243 | A1 | 11/2004 | Haefner et al. |
| 2005/0137481 | A1 | 6/2005 | Sheard et al. |
| 2005/0137626 | A1 | 6/2005 | Pastore et al. |
| 2006/0069322 | A1 | 3/2006 | Zhang et al. |
| 2006/0206267 | A1 | 9/2006 | Kirkland et al. |
| 2006/0258952 | A1 | 11/2006 | Stahmann et al. |
| 2007/0021797 | A1 | 1/2007 | Kieval et al. |
| 2007/0060797 | A1* | 3/2007 | Ball .................... A61B 5/0031 600/300 |
| 2007/0255112 | A1 | 11/2007 | Taepke, II et al. |
| 2008/0119750 | A1 | 5/2008 | Patangay et al. |
| 2008/0294209 | A1 | 11/2008 | Thompson et al. |
| 2013/0018234 | A1 | 1/2013 | Thompson et al. |

FOREIGN PATENT DOCUMENTS

| | | |
|---|---|---|
| WO | WO-2004101062 A1 | 11/2004 |
| WO | WO-2005037367 A3 | 4/2005 |
| WO | WO-2007024570 A2 | 3/2007 |

OTHER PUBLICATIONS

"U.S. Appl. No. 13/620,462, Advisory Action dated Mar. 25, 2014", 10 pgs.
"U.S. Appl. No. 13/620,462, Applicant's Summary of Examiner Interview filed Apr. 10, 2014", 1 pg.
"U.S. Appl. No. 13/620,462, Final Office Action dated Nov. 19, 2015", 17 pgs.
"U.S. Appl. No. 13/620,462, Final Office Action dated Dec. 24, 2013", 14 pgs.
"U.S. Appl. No. 13/620,462, Non Final Office Action dated Mar. 18, 2015", 14 pgs.
"U.S. Appl. No. 13/620,462, Non Final Office Action dated Jun. 5, 2013", 11 pgs.
"U.S. Appl. No. 13/620,462, Non Final Office Action dated Jul. 8, 2016", 8 pgs.
"U.S. Appl. No. 13/620,462, Non Final Office Action dated Aug. 14, 2014", 14 pgs.

(56) References Cited

OTHER PUBLICATIONS

"U.S. Appl. No. 13/620,462, Notice of Allowance dated Jan. 19, 2017", 12 pgs.
"U.S. Appl. No. 13/620,462, Response filed Jan. 5, 2016 to Final Office Action dated Nov. 19, 2015", 9 pgs.
"U.S. Appl. No. 13/620,462, Response filed Mar. 3, 2014 to Final Office Action dated Dec. 24, 2013", 10 pgs.
"U.S. Appl. No. 13/620,462, Response filed Jun. 17, 2015 to Non Final Office Action dated Mar. 18, 2015", 16 pgs.
"U.S. Appl. No. 13/620,462, Response filed Sep. 5, 2013 to Non Final Office Action dated Jun. 5, 2013", 11 pgs.
"U.S. Appl. No. 13/620,462, Response filed Sep. 26, 2016 to Non Final Office Action dated Jul. 8, 2016", 9 pgs.
"U.S. Appl. No. 13/620,462, Response filed Nov. 12, 2014 to Non Final Office Action dated Aug. 14, 2014", 9 pgs.
"Chinese Application Serial No. 200880016829.3, Office Action dated May 23, 2012", 16 pgs.
"File history for EP Application No. 08754635.4", (Mar. 15, 2011), 94 pgs.
"File History for U.S. Appl. No. 11/805,311", 314 pgs.
"International Application Serial No. PCT/US2008/006526, International Preliminary Report on Patentability dated Dec. 3, 2009", 7 pgs.
"International Application Serial No. PCT/US2008/006526, International Search Report dated Dec. 22, 2008", 3 pgs.
"International Application Serial No. PCT/US2008/006526, Written Opinion dated Dec. 22, 2008", 6 pgs.
"Japanses Application Serial No. 2010-509378, Office Action dated Mar. 27, 2012", 4 pgs.
Boyle, A, et al., "Redefining the Therapeutic Objective in Decompensated Heart Failure: Hemoconcentration as a Surrogate for Plasma Refill Rate", Journal of Cardiac Failure, vol. 12, No. 4, (2006).
Francis, et al., "Accurate Vasoconstrictor Response to IV Furosemide in Patients with Chronic Congestive Heart Failure", Annals of Internal Medicine, vol. 130, No. 1, (1985).
"U.S. Appl. No. 11/431,806, Non Final Office Action dated Mar. 18, 2010", 8 pgs.
"U.S. Appl. No. 11/431,806, Response filed Jan. 14, 2010 to Restriction Requirement dated Dec. 18, 2009", 9 pgs.
"U.S. Appl. No. 11/431,806, Response filed Jun. 18, 2010 to Non Final Office Action dated Mar. 18, 2010", 8 pgs.
"U.S. Appl. No. 11/431,806, Restriction Requirement dated Dec. 18, 2009", 9 pgs.
"U.S. Appl. No. 11/805,311, Advisory Action dated Feb. 1, 2011", 6 pgs.
"U.S. Appl. No. 11/805,311, Final Office Action dated Nov. 15, 2010", 12 pgs.
"U.S. Appl. No. 11/805,311, Final Office Action dated Nov. 29, 2011", 13 pgs.
"U.S. Appl. No. 11/805,311, Non Final Office Action dated Mar. 31, 2011", 10 pgs.
"U.S. Appl. No. 11/805,311, Non Final Office Action dated Apr. 29, 2010", 10 pgs.
"U.S. Appl. No. 11/805,311, Notice of Allowance dated Jan. 23, 2012", 8 pgs.
"U.S. Appl. No. 11/805,311, Notice of Allowance dated May 25, 2012", 8 pgs.
"U.S. Appl. No. 11/805,311, Response filed Jan. 12, 2011 to Final Office Action dated Nov. 15, 2010", 11 pgs.
"U.S. Appl. No. 11/805,311, Response filed Jan. 25, 2010 to Restriction Requirement dated Dec. 24, 2009", 8 pgs.
"U.S. Appl. No. 11/805,311, Response filed Mar. 15, 2011 to Advisory Action dated Feb. 1, 2011", 11 pgs.
"U.S. Appl. No. 11/805,311, Response filed Jul. 27, 2010 to Non Final Office Action dated Apr. 29, 2010", 9 pgs.
"U.S. Appl. No. 11/805,311, Response filed Aug. 31, 2011 to Non Final Office Action dated Mar. 31, 2011", 12 pgs.
"U.S. Appl. No. 11/805,311, Response filed Dec. 21, 2011 to Final Office Action dated Nov. 29, 2011", 7 pgs.
"U.S. Appl. No. 11/805,311, Restriction Requirement dated Dec. 24, 2009", 9 pgs.
"Chinese Application Serial No. 200880016829.3, Office Action dated Mar. 4, 2013", 2 pgs, English Translation.
"Chinese Application Serial No. 200880016829.3, Response filed May 20, 2013 to Office Action dated Mar. 4, 2013", With English Claims, 9 pgs.
"European Application Serial No. 08754635.4, Examination Notification Art. 94(3) mailed Apr. 27, 2010", 3 pgs.
"European Application Serial No. 8754635.4, Decision of grant dated Jun. 11, 2015", 2 pgs.
"European Application Serial No. 8754635.4, Examination Notification Art. 94(3) mailed Apr. 27, 2010", 3 pgs.
"European Application Serial No. 8754635.4, Office Action dated Jan. 26, 2010", 2 pgs.
"European Application Serial No. 8754635.4, Response filed Mar. 15, 2010 to Office Action dated Jan. 26, 2010", 23 pgs.
"European Application Serial No. 8754635.4, Response filed Oct. 11, 2010 to Examination Notification Art. 94(3) mailed Apr. 27, 2010", 7 pgs.

\* cited by examiner

DECONGESTIVE THERAPY TITRATION FOR HEART FAILURE PATIENTS USING IMPLANTABLE SENSOR

CLAIM OF PRIORITY

This application is a continuation of U.S. patent application Ser. No. 13/620,462, filed on Sep. 14, 2012, now issued as U.S. Pat. No. 9,655,520, which is a divisional of U.S. patent application Ser. No. 11/805,311, filed on May 23, 2007, now issued as U.S. Pat. No. 8,271,080, each of which is hereby incorporated herein by reference.

FIELD OF THE INVENTION

The present invention relates generally to therapy management and, more particularly, to determining if a target level of therapy benefit has been achieved using sensor data acquired via a medical device, such as an implantable medical device.

BACKGROUND OF THE INVENTION

Day-to-day management of patients with various diseases and disorders, such as chronic heart failure (HF), requires accurate clinical assessment of the patient's condition. The complex neurohormonal mechanisms that are activated by left ventricular (LV) dysfunction, for example, can lead to fluid volume overload and increase in LV filling pressure. This may be exacerbated by minor changes in salt and water intake, anemia, and changes in a drug regimen. The changes often cause cardiac decompensation and accumulation of fluid in lungs, leading to costly hospitalizations and progressive worsening of heart failure. Timely clinical intervention may prevent worsening of a patient's HF status, requiring accurate and timely assessment of patient state.

An HF patient typically takes a multitude of drugs to alleviate symptoms and control the disease progression. The therapy targets vary between drugs and patients. For example, drugs that lead to neurohormonal improvement (e.g., Beta-blockers, ACE-inhibitors) should be titrated to the target dosage. Diuretics, on the other hand, need to be optimized on a continuous basis to maintain hemodynamic balance.

SUMMARY OF THE INVENTION

The present invention is directed to systems and methods for assessing a therapy delivered to a heart failure patient. Embodiments of the present invention provide for sensing, from within the patient, a physiologic parameter indicative of the patient's status responsive to the therapy, and determining if a target level of therapy benefit to the patient has been achieved based on a relationship between the sensed physiologic parameter and a threshold developed for the patient. A first output may be produced in response to determining that the target level of patient benefit has been achieved and a second output may be produced in response to determining that the patient is subject to over-therapeuting. The therapy may comprise one or more of a drug therapy, a neurostimulation therapy, and a cardiac electrical stimulation therapy.

Embodiments of the present invention may provide for assessing decongestive therapy delivered to a heart failure patient, which may involve sensing, from within the patient, a physiologic parameter indicative of the patient's diuresis status, determining if a target level of patient diuresis has been achieved based on a relationship between the sensed physiologic parameter and a threshold developed for the patient, and producing an output in response to determining that the target level of patient diuresis has been achieved.

The relationship between the sensed physiologic parameter and the threshold may include at least one of the sensed physiologic parameter returning to a baseline value established as the threshold, the sensed physiologic parameter returning to a predetermined percentage or function of a baseline value established as the threshold, a rate of change of increase or decrease of the sensed physiologic parameter relative to the threshold, a rate of change of increase or decrease of the sensed physiologic parameter relative to a sate level of patient diuresis established as the threshold, and a change of the sensed physiologic parameter that matches a response of the physiologic parameter associated with a prior successful therapy delivered to the patient.

The physiologic parameter indicative of the patient's diuresis status may comprise at least one of a thoracic fluid parameter, a thoracic impedance parameter, a heart sounds parameter, a cardiac chamber pressure parameter, an arterial pressure parameter, a respiration parameter, heart rate parameter, heart rate variability parameter, an electrogram conduction pattern parameter, a blood chemistry parameter, a potassium level parameter, a blood perfusion parameter, a blood oxygen saturation parameter, a body extremity temperature parameter, a body extremity perspiration parameter, and a patient weight parameter. The threshold may be established by a physician.

Methods may further involve detecting an occurrence of a congestive event, and sensing the physiologic parameter in response to detection of the congestive event. Methods of the present invention may be performed for chronic diuretic therapy and acute management of emergent diuretic therapy responsive to a congestive event.

Embodiments of the present invention may provide for titrating the decongestive therapy based on the produced output. An alert may be generated in response to one or more of detecting over-diuresis of the patient, detecting non-compliance to a drug regimen of the decongestive therapy, and detecting refractoriness to the decongestive therapy.

Methods of the present invention may be performed in real-time during delivery of the decongestive therapy. Embodiments may involve adjusting sensing of the physiologic parameter based on one or more of a type of medication administered to the patient for decongestive therapy, a manner of delivering the decongestive therapy, and one or more patient specific conditions. Methods of the present invention may be performed entirely within a patient or partially within the patient, such in cooperation with a patient-external system or device.

According to various embodiments, systems for assessing decongestive therapy delivered to a heart failure patient preferably include an implantable sensor configured to sense a physiologic parameter indicative of the patient's diuresis status and a processor coupled to the implantable sensor. The sensor may comprise a thoracic fluid sensor, a heart sounds sensor, a cardiac chamber or arterial pressure sensor, a respiration sensor, or a blood chemistry sensor, for example. The processor is preferably configured to determine if a target level of patient diuresis has been achieved based on a relationship between the sensed physiologic parameter and a threshold developed for the patient, and to produce an output in response to determining that the target level of patient diuresis has been achieved.

The processor may be disposed in an implantable housing. The processor may be disposed in a housing external to the patient. The processor may be a processor of a network server system. The processor may be configured to generate an alert signal in response to one or more of detecting over-diuresis of the patient, detecting non-compliance to a drug regimen of the decongestive therapy, and detecting refractoriness to the decongestive therapy.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
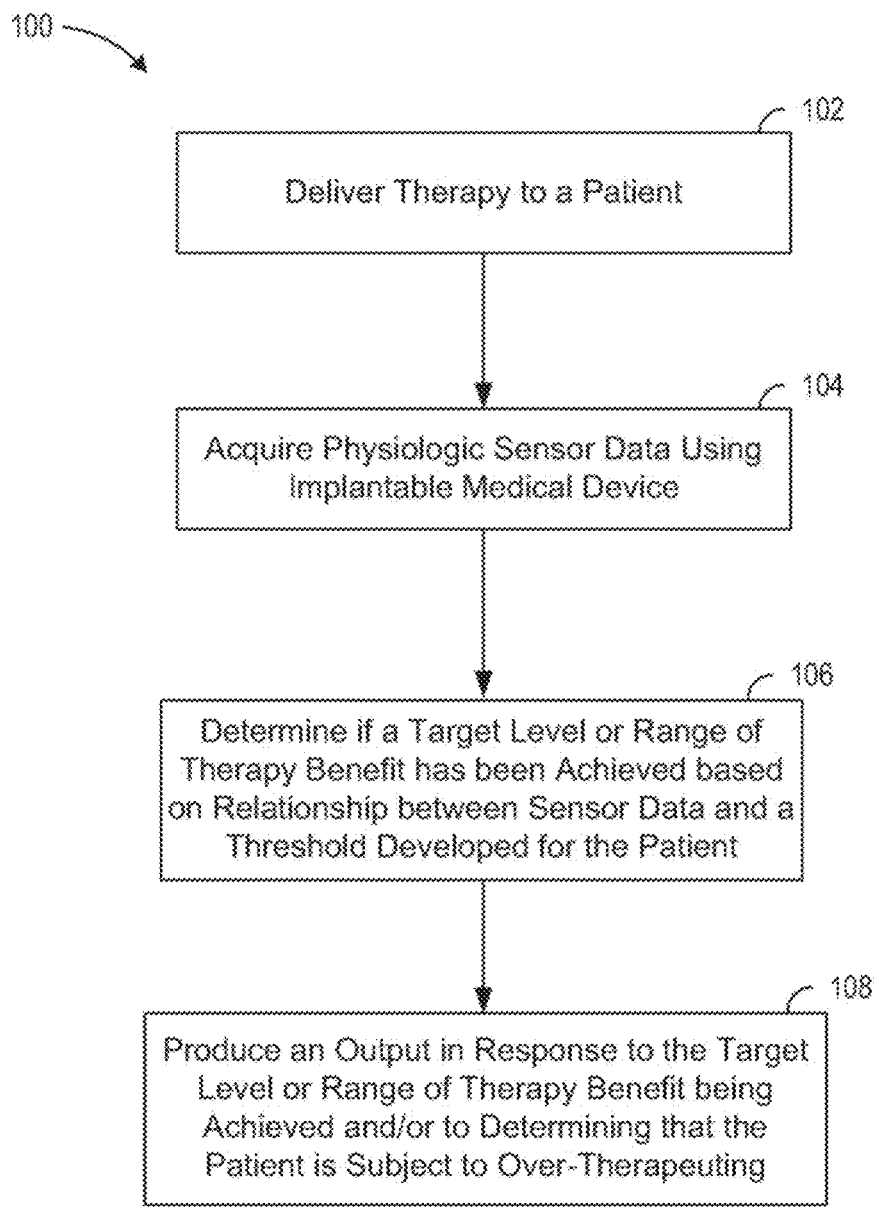
FIG. 1A is a flow diagram of a method for assessing a therapy delivered to a heart failure patient using an implantable sensing device in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A medical device according to the present invention may include one or more of the features, structures, methods, or combinations thereof described hereinbelow. For example, a status monitor, cardiac monitor, cardiac stimulator, or other type of implantable or patient-external medical device may be implemented to include one or more of the advantageous features and/or processes described below. It is intended that such a monitor, stimulator, or other external, implanted or partially implanted device need not include all of the features described herein, but may be implemented to include selected features that provide for useful structures and/or functionality. Such a device may be implemented to provide a variety of therapeutic or diagnostic functions.

A wide variety of implantable medical devices, such as cardiac sensing and/or stimulation devices, may be configured to implement a therapy assessment methodology of the present invention. A non-limiting, representative list of such devices includes cardiac monitors, pacemakers, cardioverters, defibrillators, resynchronizers, and other cardiac sensing and therapy delivery devices. These devices may be configured with a variety of electrode arrangements, including surface, transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

A variety of devices other than cardiac monitoring/stimulation devices may also be implemented to provide for therapy assessment, such as external and implantable drug delivery devices equipped with an external or implantable physiologic sensor or nerve stimulation devices equipped with an implantable or external physiologic sensor, for example. Such devices are referred to herein generally as a patient-implantable medical device (PIMD) for convenience, it being understood that such a medical device may alternatively be implemented at least in part as a patient-external medical device.

The present invention is directed to systems and methods for assessing a heart failure patient's response to a therapy and tailoring it thereafter. Embodiments of the present invention are directed to systems and methods for assessing an HF patient's response to decongestive therapy and tailoring it thereafter. Accurate dosing of decongestive therapy in HF patients is known to be a difficult but important part of HF patient management. It is important to balance the therapeutic need for fluid removal during acute decongestion with the potential risks associated with over-diuresis. Presently, there is little evidence-based information to guide the management of decongestive therapy.

Heart failure patients typically require a combination of therapies in order to improve their disease state. Conventional therapies fall into various classes, some of which are proven to provide mortality benefit (e.g., Beta-blockers, ACE-Is, ARBs) and some that provide mostly symptomatic relief without any proven mortality benefit (e.g., diuretics). Use of loop diuretics, which fall in the latter class of therapies/medications, has an associated risk of exacerbating the patient's heart failure status through activation of deteriorating systems such as the Renin-Angiotensin-Aldosterone-System (RAAS), although it is usually the first line of defense used to treat HF patients. Subsequently, it may become important to maintain HF patients on a target or optimal dose of these therapies that provide an effective response (e.g., fluid reduction in the case of diuretics) yet without over-medicating the patient. More importantly, when HF patients are decompensated, this balance becomes more imperative as the patients can further deteriorate very quickly.

Embodiments of the present invention provide for implantable device-based sensor information to guide diuresis to achieve a desired or optimal level of decongestion. In general, a desired or optimal level of decongestion may be indicated by a signal target value or multiple target values, such as a range of target values. A desired or optimal level of decongestion may be indicated by qualitative factors, such as a level of patient well-being indicating that a desired or optimal level of decongestion has been achieved. Such qualitative factors may be determined by the clinician, the patient, or both, such as by use of a survey or questionnaire (e.g., an electronic questionnaire implemented by use of a networked advanced patient management system).

According to various embodiments, sensors are deployed, at least some of which are preferably implanted in an HF patient, to monitor patient status in real-time during the application of decongestive therapy, and may provide feedback as to when decongestive therapy should be terminated. Device-based sensors may provide objective information to a physician or clinician in order to prevent over-diuresis. One or more sensors may be configured to monitor certain physiological parameters (e.g., thoracic fluid via thoracic impedance or other sensor, heart sounds, cardiac chamber or pulmonary atrial pressure, respiration, heart rate, heart rate variability, electrogram conduction pattern, blood chemistry, blood pressure, potassium sensor, blood perfusion, blood oxygen saturation, body or limb temperature, body or limb perspiration, patient weight) for the change elicited by the diuretic therapy and relay this information to the physician or clinician for immediate responsive action. Various system embodiments may include those that incorporate one or more implantable sensors, one or more patient-external sensor, or a combination of internal and patient-external sensors.

Providing a clinician or physician with real-time sensor information indicative of the patient's response to decongestive therapy permits the clinician or physician to better understand the patient's individual drug response and facilitates optimization of the patient's drug regimen. In the absence of such timely response data made available by embodiments of the present invention, the clinician or physician is limited to traditional techniques of adjusting drug dosages and/or frequency of delivery based on judgment and/or professional norms. Hence, providing physicians with timely sensor data reflective of a patients diuresis state in response to decongestive therapy overcomes problems associated with conventional drug titration approaches by providing objective data from which physicians/clinicians may gain access to an individual patient's physiologic state, and allows for the effective titration of a drug therapy being delivered to the patient and avoidance of over-medicating the patient.

Turning now to FIG. 1A, there is illustrated a method 100 of assessing a patient's response to a therapy in accordance with embodiments of the present invention. According to the method 100 shown in FIG. 1A, a therapy is delivered to, or taken by (e.g., oral drugs), a patient 102. The therapy is typically a drug therapy (e.g., diuretic or decongestive therapy), but may also be or include a neurostimulation or cardiac electrical stimulation therapy. Sensor data is acquired 104 using a medical device, which is preferably an implantable device but may alternatively be a patient-external device. The sensor data reflects a response to the drug therapy by the patient. A determination 106 is made as to whether a target level of therapy benefit has been achieved based on a relationship between the sensor data and a threshold preferably developed for the patient. For example, a determination may be made as to whether the patient is being subject to under- and/or over-therapeuting. An output is produced 108 in response to the target level of therapy benefit being achieved and/or to determining that the patient is subject to over-therapeuting.

Figure 1B:
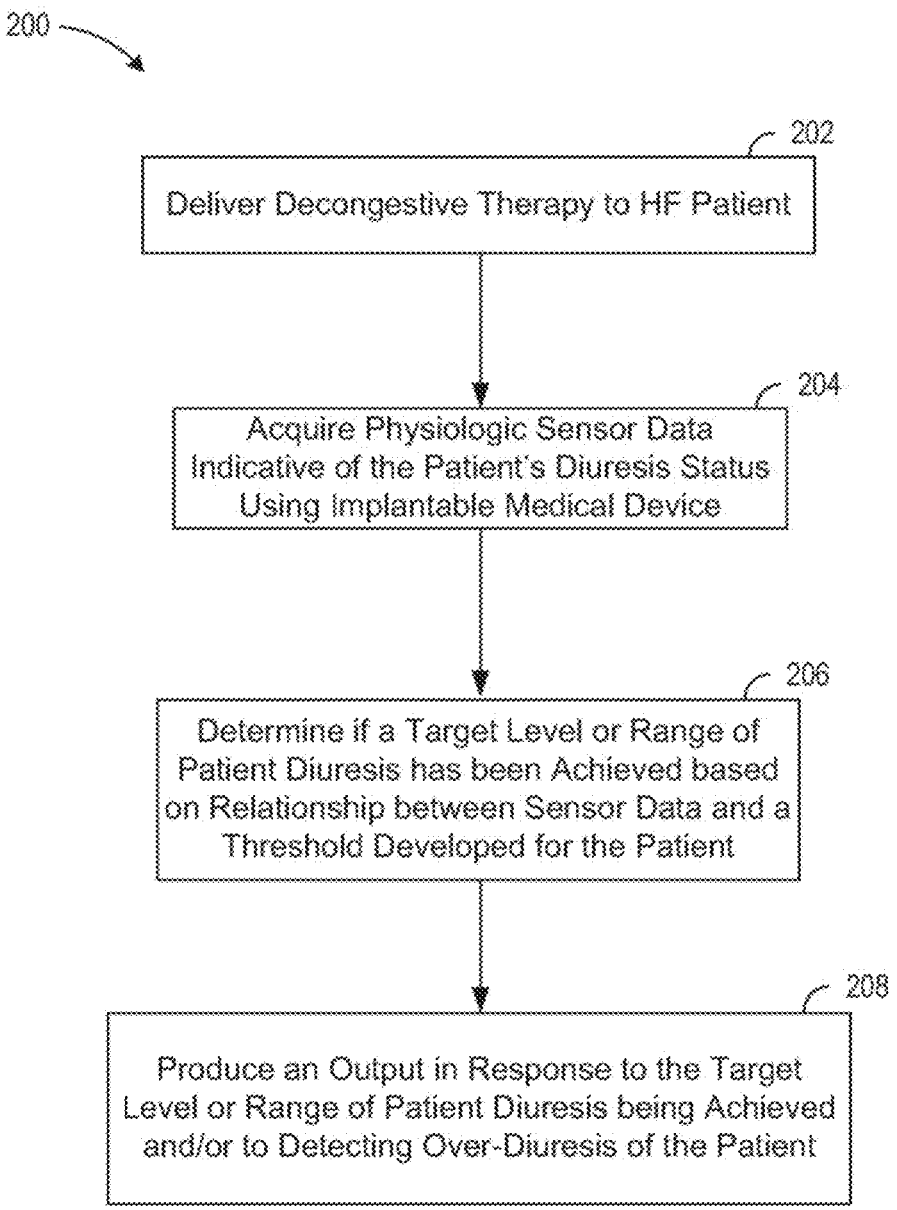
FIG. 1B is a flow diagram of a method for assessing a decongestive therapy delivered to a heart failure patient using an implantable sensing device in accordance with embodiments of the present invention.

FIG. 1B illustrates a method 200 of assessing a heart failure patient's response to decongestive drug therapy in accordance with embodiments of the present invention. According to the method 200, a decongestive therapy is delivered 202 to an HF patient. Sensor data indicative of the patient's diuresis status is acquired 204 using a medical device, preferably an implantable medical device-based sensor, but may alternatively be a patient-external device. According to various embodiments, an occurrence of a congestive event may be detected using one or more sensors, and sensing of the physiologic parameter may commence in response to detection of the congestive event.

A determination 206 is made as to whether a target level of patient diuresis has been achieved based on a relationship between the sensor data and a threshold preferably developed specifically for the patient. For example, a determination may be made as to whether the patient is being subject to under- and/or over-diuresis. An output is produced 208 in response to the target level of patient diuresis being achieved and/or to detecting over-diuresis of the patient.

Non-optimal levels of diuresis therapy (e.g., levels below or beyond a target level or range) may be determined in several ways. For example, the physician may identify optimal patient's state and the device may be configured to identify the sensor level which corresponds to the physician identified optimal patient state. Optimal patient state may be indicated based on one or more of the physiologic conditions or sensor outputs discussed herein, such as a drop in blood pressure, decreased perfusion to the extremities (e.g., cold and dry), and excessive potassium loss (which may be indicated by a blood chemistry sensor or detection of arrhythmias via electrical cardiac signal analysis).

The method 200 shown in FIG. 1B is preferably performed in real-time under stable conditions and during delivery of the decongestive therapy. The method 200 may be performed entirely or at least in part within the patient using an implantable device and sensor(s). The method 200 may alternatively be performed entirely or at least in part externally of the patient in certain embodiments. For example, acquiring physiologic sensor data 204 may be performed within the patient. Determining 206 if the target level of patient diuresis has been achieved and producing an output 208 in response to the target level of patient diuresis being achieved may respectively be performed within the patient or externally of the patient.

As is indicated in box 206 in FIG. 1B, determining whether a target level of patient diuresis has been achieved is preferably based on a relationship between the sensor data and a threshold preferably developed specifically for the patient. The threshold may be established in several ways. According to one approach, a physician may determine the target level of diuresis based on the patient's HF status, overall condition, and other relevant factors. The target level may be established as the threshold for the particular patient. The threshold value may be transferred from the physician to the medical device via a programmer or other communication device, typically via a wireless link. Target levels associated with a particular patient may include, for example, a physician indicated target blood pressure and/or weight target. As previously discussed, such targets may be represented by a single value or a ranges of values, and such targets may include one or both of quantitative and qualitative targets (e.g., patient well being targets). A threshold developed for a class or population of HF patients may also be used.

The relationship between the sensed physiologic parameter and the threshold indicated in box 206 may take several forms. For example, the relationship between the sensed physiologic parameter and the threshold may be defined as the sensed physiologic parameter returning to a baseline value. The relationship between the sensed physiologic parameter and the threshold may be defined as the sensed physiologic parameter returning to a predetermined percentage or function of a baseline value. By way of further example, the relationship between the sensed physiologic parameter and the threshold may be defined as a rate of change of increase or decrease of the sensed physiologic parameter relative to the threshold. The relationship between the sensed physiologic parameter and the threshold may also be defined as a rate of change of increase or decrease of the sensed physiologic parameter relative to a safe level of patient diuresis. Also, the relationship between the sensed physiologic parameter and the threshold may be defined as a change of the sensed physiologic parameter that matches a response of the physiologic parameter associated with a prior successful therapy delivered to the patient.

The physiologic sensor data acquired in box 204 may include data developed using a wide range of sensors, including implantable device-based sensors. For example, the physiologic sensor data may comprises at least one of a thoracic fluid parameter (e.g., such as derived using a thoracic impedance sensor), a heart sounds parameter, a cardiac chamber or arterial pressure parameter, a respiration parameter, a heart rate parameter, a heart rate variability parameter, a blood chemistry parameter, and an electrogram conduction pattern parameter, among others. Also, sensing of one or more physiologic sensor data parameters may be adjusted based on one or more of a type of medication administered to the patient for decongestive therapy, a manner of delivering the decongestive therapy (e.g., intravenous or oral, and one or more patient specific conditions.

Figure 2:
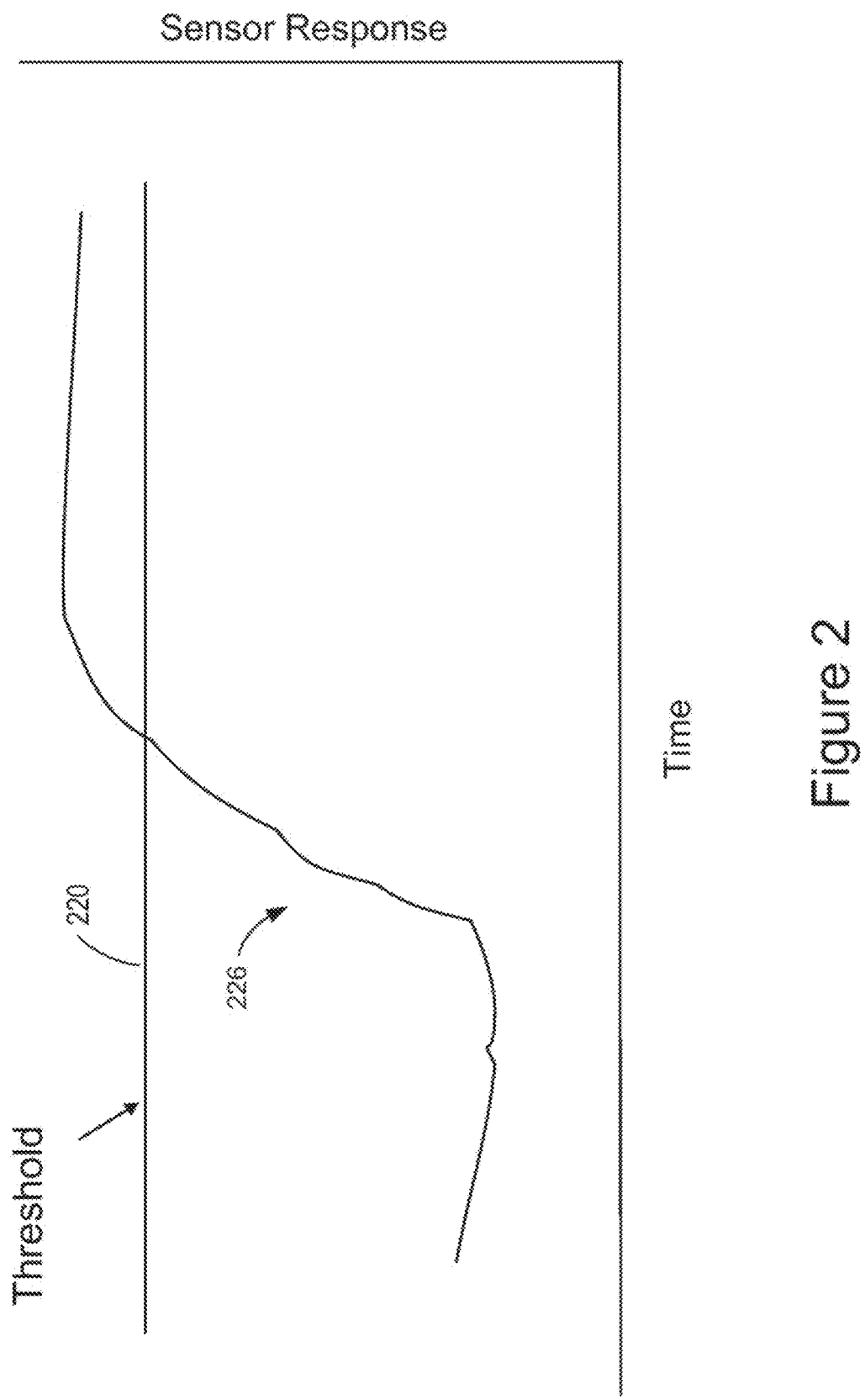
FIG. 2 illustrates changes of a physiologic parameter (e.g., thoracic impedance) in response to delivery of decongestive therapy as sensed by an implantable device in accordance with other embodiments of the present invention.

FIG. 2 illustrates changes of a physiologic parameter responsive to delivery of a decongestive therapy for a patient as sensed by an implantable device in accordance with embodiments of the present invention. A sensor response signal 226 is monitored to determine if the signal 226 reaches a threshold 220, where reaching the threshold 220 represents that an optimal or desirable level of therapy has been achieved. The therapy is preferably titrated over time so that the sensor response signal 226 settles at or close to the threshold 220. The signal 226 may be any of the physiologic signals discussed herein, preferably produced by an implantable sensor.

Although a single signal waveform is shown in FIG. 2 for purposes of clarity, it is understood that multiple sensor response signals may be acquired and monitored from any number and type of sensors. Moreover, FIG. 2 may further include a plot of drug doses (e.g., time and amount of delivery) to facilitate clinician assessment of the patient's response to the drug therapy. FIG. 2 may, for example, include plots of different sensor response signals each associated with a different drug or other decongestive or HF therapy parameter. Changes in patient weight may also be plotted in FIG. 2, which may be acquired automatically or manually (e.g., via an electronic or mechanical bed scale).

According to embodiments of the present invention, the sensor response signal 226 may be indicative of changes in thoracic impedance (y-axis) plotted over units of time (x-axis), such as minutes or hours, for a patient's response to repeated diuretic intervention. If desired, the plot in FIG. 2 may further show a mean impedance signal developed for the patient using an implanted thoracic impedance sensor in the absence of drug delivery and a congestive event. Curve 226 shows changes in thoracic impedance in response to delivery of a diuretic.

The threshold 220 is preferably established for the patient, as previously discussed. The threshold 220, in this illustrative example, may represent a target level of thoracic impedance indicative of a target level of thoracic fluid as determined by the physician. Using physiologic data acquired from the patient, decongestive therapy can be titrated so that a desired or optimal level of patient diuresis is achieved, as can be readily seen in the data plotted in FIG. 2.

Figure 3:
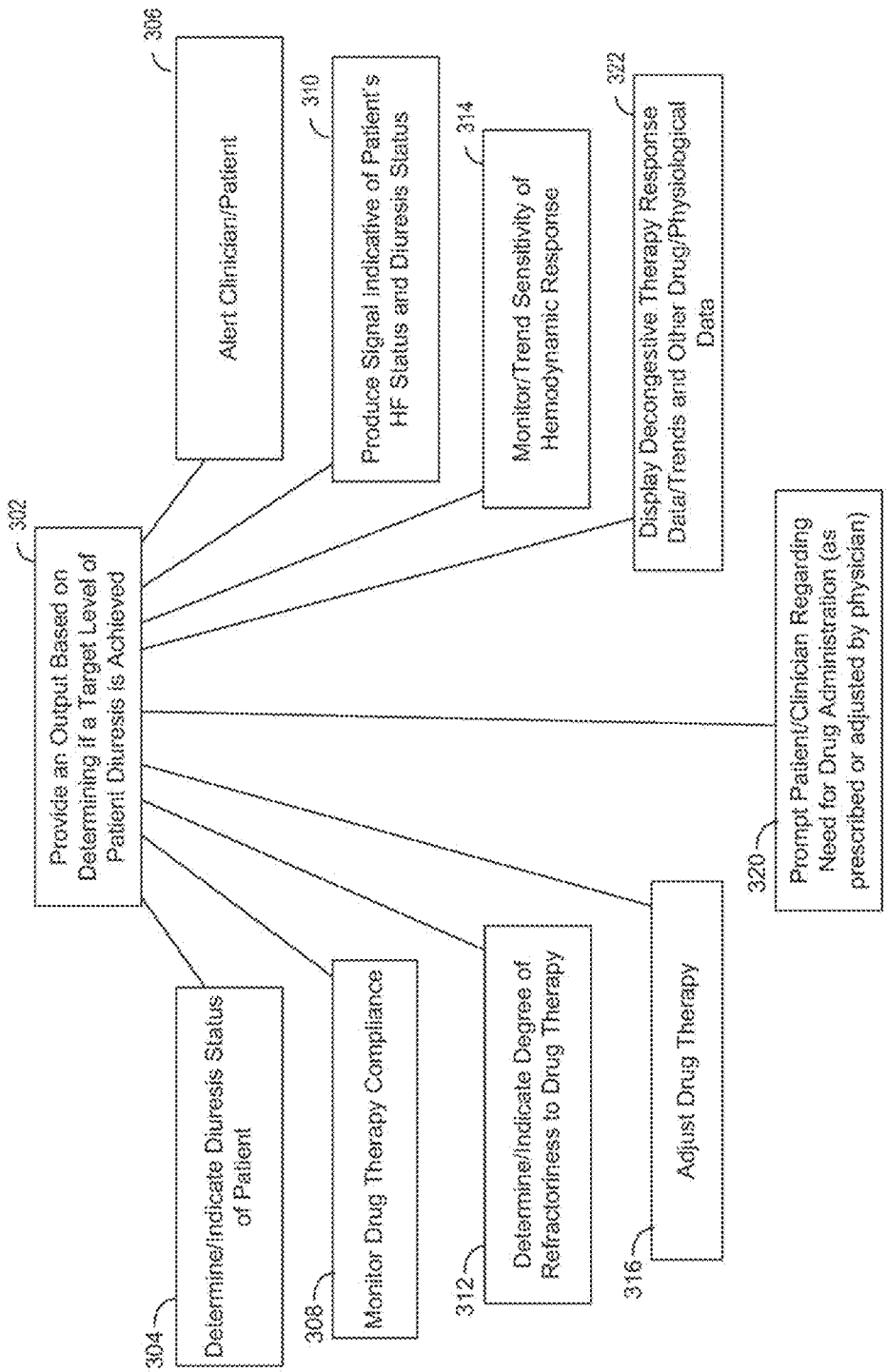
FIG. 3 is a block diagram showing a variety of illustrative operations that may be performed in response to an output indicative of a patient's response to a drug therapy in accordance with embodiments of the present invention.

FIG. 3 is a block diagram showing a variety of illustrative operations that may be performed by systems and methods of assessing decongestive therapy for an HF patient in accordance with embodiments of the present invention. As is shown in FIG. 3, an output from an algorithm that implements a methodology for assessing decongestive therapy for an HF patient is provided 302 based on a determination of whether or not a target level of patient diuresis has been achieved. This output may take various forms and be used for a variety of purposes. The output may be produced by a medical device implanted within the patient. The output may also be produced by a patient-external device that receives sensor data from a medical device implanted within the patient. Other output scenarios are contemplated.

As is shown in FIG. 3, the diuresis status of the patient may be determined or indicated 304 using the output 302. An alert to the clinician and/or patient 306 may be generated and communicated in various forms to the clinician and/or patient in response to the output 302, such as in response to detecting over-diuresis of the patient. Drug therapy compliance by the patient, clinician or caregiver may be monitored 308 using the output 302. Signals indicative of the patient's HF status and diuresis status may be produced 310 and take several forms, including electrical or electromagnetic signals, optical signals, or acoustic signals, for example.

A degree of patient refractoriness to the drug therapy may be determined or indicated 312 based on the output 302. A sensitivity of the patient's response to the decongestive therapy may also be determined or indicated. The decongestive therapy may be adjusted or titrated 316 as discussed above. Statistical analyses of the patient's decongestive therapy response data may be initiated or performed in response to the output 302.

The patient, caregiver, and/or clinician may be prompted 320, such as by audible, textual, or visual means, as to the need for drug administration as originally prescribed or adjusted by the physician based on the output 302. A patient's sensitivity of response to the decongestive therapy may be monitored and/or trended 314. A variety of response data, trend data, and other drug and physiological data may be displayed 322 for use by the patient, caregiver, clinician, and/or physician. FIG. 3 is intended to provide a non-exhaustive, non-limiting listing of examples concerning the use of output information 302 developed from one or more sensors of an implantable or patient-external medical device in accordance with the principles of the present invention.

Figure 4:
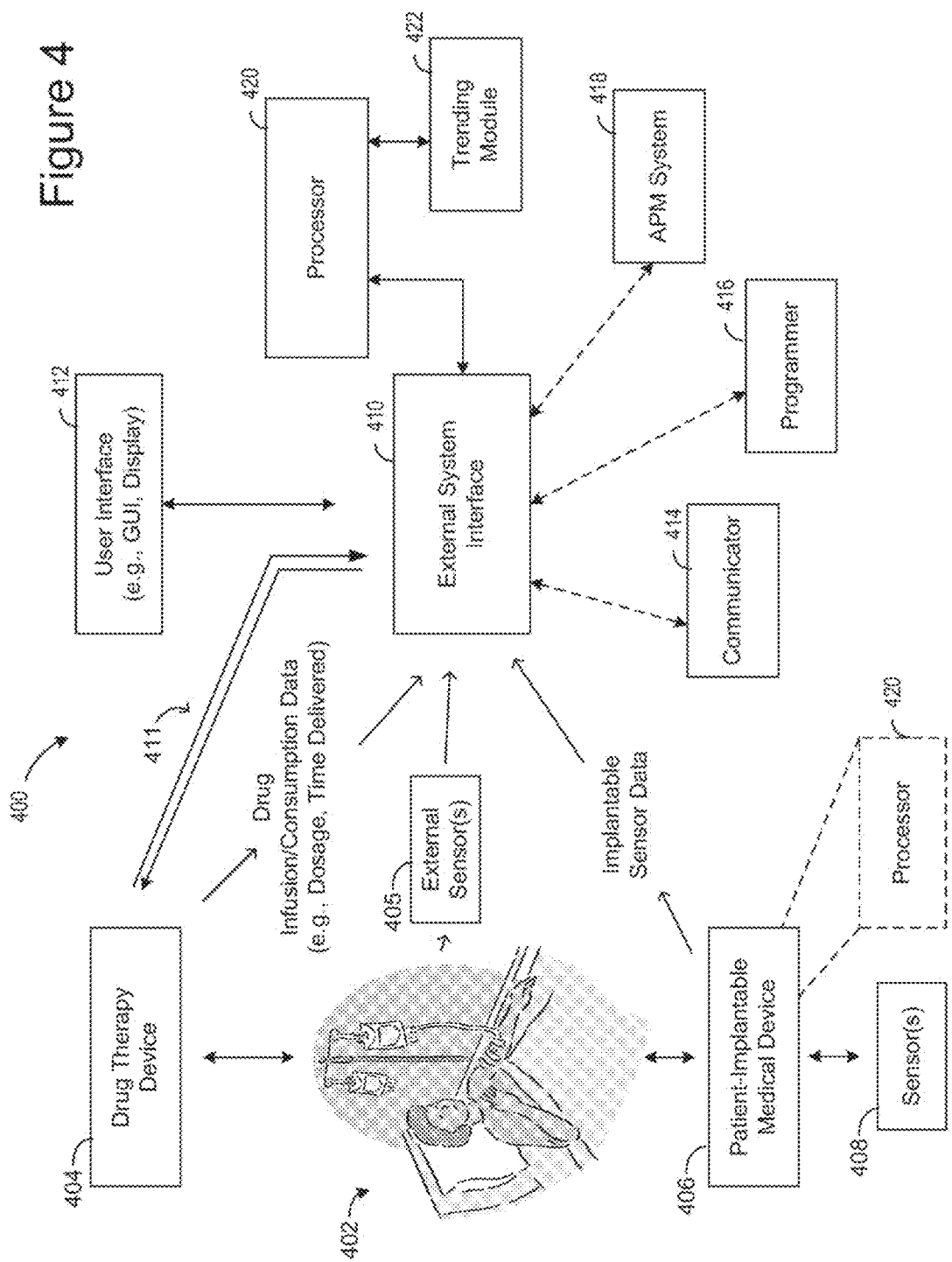
FIG. 4 is a block diagram of a system for assessing a therapy delivered to a patient based on implantable sensor data acquired from the patient in accordance with embodiments of the present invention.

FIG. 4 is a block diagram of a system 400 for managing patient drug delivery based on a response of the patient to the drug delivery in accordance with embodiments of the present invention. FIG. 4 shows a patient 402 that is receiving drug therapy as prescribed by a physician. The drug therapy may be delivered to the patient 402 by infusion using a drug therapy device 404, such as a drug pump device. The drug therapy may also be delivered by patient consumption of the prescribed medication, in which case the drug therapy device 404 may represent a pill counting device or drug consumption questionnaire, for example.

The system 400 shown in FIG. 4 includes a patient-implantable medical device 406 that is implanted in the patient 402. PIMD 402 incorporates or is coupled to one or more implantable sensors 408. One or more of the sensors 408 are configured to sense a physiologic parameter or condition of the patient. Such sensors 408 may include one or more of a thoracic impedance sensor (e.g., implanted transthoracic total impedance sensor), a blood (internal filling) pressure sensor, blood flow sensor, blood perfusion sensor (e.g., plethysmography sensor), blood temperature sensor, blood gas sensor (e.g., oximeter sensor), heart sounds sensor (e.g., accelerometer or microphone), and blood chemistry or composition sensor $PO_2$ sensor, $SAO_2$ sensor, glucose sensor, potassium sensor, lactate sensor, $PCO_2$ sensor, pH sensor, and molecular probe). Examples of suitable blood (internal filling) pressure sensors, blood flow sensors, blood temperature sensors, and associated detection techniques are described in commonly-owned U.S. Pat. Nos. 6,666,826 and 6,892,095, which are hereby incorporated herein by reference.

A variety of external sensors 405 may also be used to sense various physiological parameters of the patient. Such external sensors 405 may include one or more of a pulse oximetry sensor, blood pressure sensor, blood chemistry sensor, patient temperature sensor, patient perspiration sensor, patient weight sensor, EKG sensor arrangement, among others.

The system 400 includes a number of patient-external devices. An external system interface 410 includes communication circuitry configured to effect communications with PIMD 406. External system interface 410 may also be configured to effect communications with the drug therapy device 404, such as by a unidirectional or bi-directional communication link. External system interface 410 may further be configured to effect communications with external sensors 405.

Uni-directional communications facilitates the transfer of drug therapy information (e.g., drug type, dosage, day/time of administration) from the drug therapy device 404 to the external system interface 410. It is understood that the external system interface 410 may be integral to, or separate from, the drug therapy device 404 in various embodiments. Bi-directional communications facilitates closed-loop management of the patient's drug therapy, which preferably allows for physician input/intervention within the loop established between the drug therapy device 404 and PIMD 406. This system configuration advantageously allows for automatic or semi-automatic titration of a drug therapy delivered to a patient.

The external system interface 410 may be communicatively coupled to, or integral with, one or more of a programmer 416, an advanced patient management system 418, a portable or hand-held communicator 414, or other patient-external system. The external system interface 410 is coupled to a user interface 412, such as a graphical user interface or other interface that provides a display. User interface 412 preferably includes a user actuatable input/output device, such as a keyboard, touch screen sensor, mouse, light pen, and the like. The user interface 412 may be used to input drug therapy information, such as type of drug(s) being administered, dosage of such drugs, times and dates of drug administration, patient information, including patient weight, perception of wellness, and other information relevant to the patient's condition or drug regimen. The user interface 412 may also be used to input one or more thresholds developed for the patient, such as threshold 220 shown in FIG. 2.

A processor 420 is shown coupled to the external system interface 410. Alternatively, processor 420 may be incorporated as a component of the PIMD 406, as is shown in phantom. The processor 420 may also be incorporated as a component of the communicator 414, programmer 416, or APM system 418. The processor 420 performs the various processes described above and provides patient response to therapy data to the external system interface 410 for display to the physician, clinician, and/or patient via the user interface 412, for example.

Various embodiments described herein may be used in connection with devices that provide for HF monitoring, diagnosis, and/or therapy. A patient implantable medical device or PIMD of the present invention may incorporate HF features involving dual-chamber or bi-ventricular pacing/therapy, cardiac resynchronization therapy, cardiac function optimization, or other HF related methodologies. For example, a PIMD of the present invention may incorporate features of one or more of the following references: commonly owned U.S. Pat. Nos. 6,411,848; 6,285,907; 4,928,688; 6,459,929; 5,334,222; 6,026,320; 6,371,922; 6,597,951; 6,424,865; 6,542,775; and 7,260,432, each of which is hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of the present invention, are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference.

A PIMD in accordance with the present invention may implement diagnostic and/or monitoring functions as well as provide cardiac stimulation therapy. Examples of cardiac monitoring circuitry, structures and functionality, aspects of which may be incorporated in a PIMD of the present invention, are disclosed in commonly owned U.S. Pat. Nos. 5,313,953; 5,388,578; and 5,411,031, which are hereby incorporated herein by reference.

Figure 5:
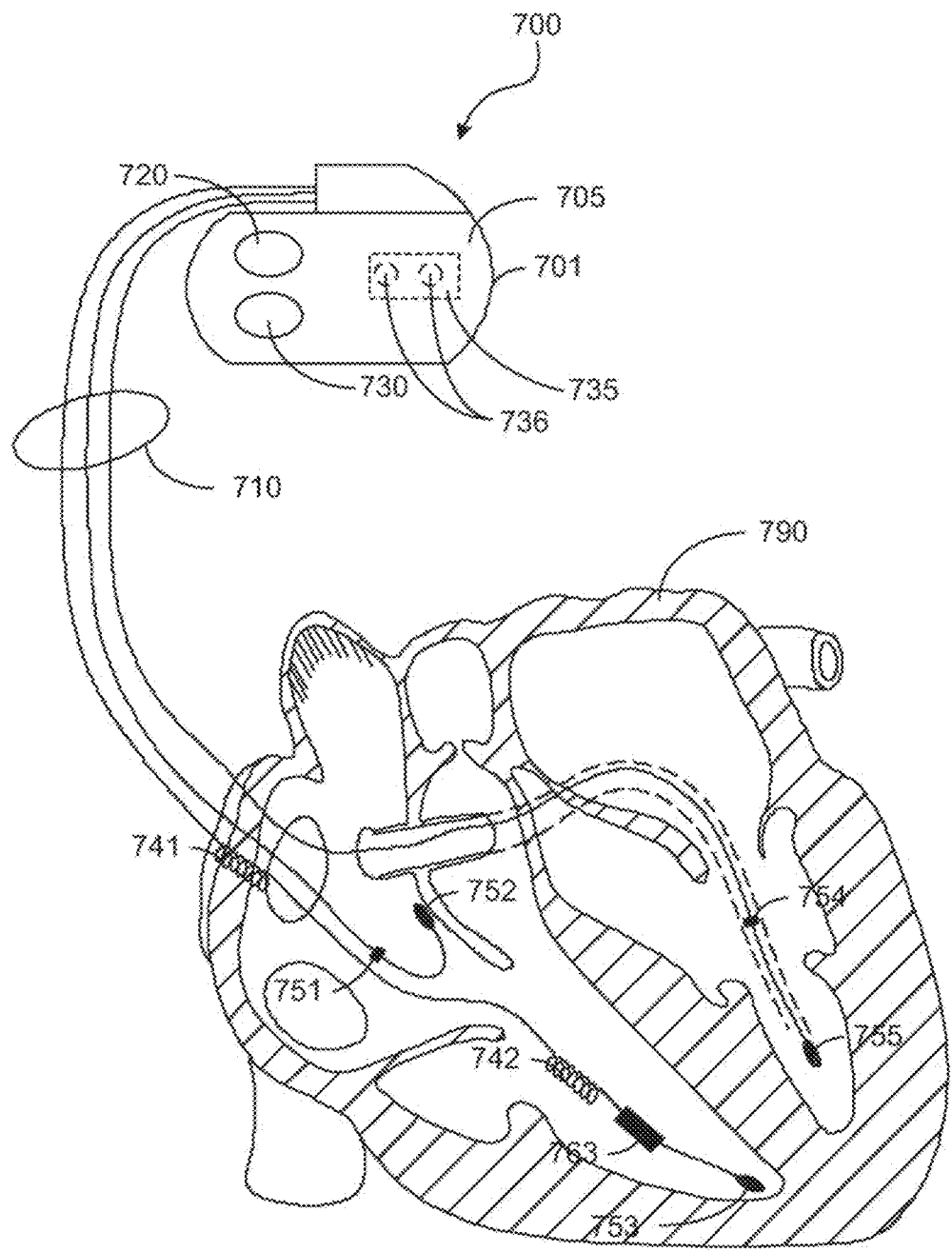
FIG. 5 is an illustration of an implantable cardiac device including a lead assembly shown implanted in a sectional view of a heart, the implantable cardiac device implemented to sense one or more physiologic parameters of a patient in accordance with embodiments of the invention.

Referring now to FIG. 5, there is illustrated an embodiment of a PIMD configured to sense one or more physiologic parameters for purposes of assessing decongestive therapy for an HF patient in accordance with embodiments of the present invention. In this illustrative example, the PIMD includes a cardiac rhythm management device (CRM) 700 including an implantable pulse generator 705 electrically and physically coupled to an intracardiac lead system 710.

Portions of the intracardiac lead system 710 are inserted into the patient's heart 790. The intracardiac lead system 710 includes one or more electrodes and/or sensors configured to sense electrical cardiac activity of the heart, deliver electrical stimulation to the heart, sense the patient's transthoracic impedance or transthoracic total impedance, sense blood (internal filling) pressure, blood flow, and/or blood temperature, sense acceleration and/or body acoustics, and/or sense other physiological parameters. Portions of the housing 701 of the pulse generator 705 may optionally serve as a can electrode.

Communications circuitry is disposed within the housing 701 for facilitating communication between the pulse generator 705 and an external communication device, such as a portable or bed-side communication station, patient-carried/worn communication station (e.g., communicator), external programmer or advanced patient management system interface, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may optionally incorporate a motion detector 720 that may be used to sense patient activity as well as various respiration and cardiac related conditions. For example, the motion detector 720 may be optionally configured to sense snoring, activity level, and/or chest wall movements associated with respiratory effort, for example. The motion detector 720 may be implemented as an accelerometer positioned in or on the housing 701 of the pulse generator 705. For a motion sensor implemented as an accelerometer, the motion sensor may also provide respiratory, e.g. rales, coughing, and cardiac, e.g. S1-S4 heart sounds, murmurs, and other acoustic information. An accelerometer may be used to develop respiration waveforms from which various respiratory parameters may be developed.

The lead system 710 and pulse generator 705 of the CRM 700 may incorporate one or more transthoracic impedance sensors that may be used to acquire the patient's respiration waveform, or other respiration-related information. The transthoracic impedance sensor may include, for example, one or more intracardiac electrodes 741, 742, 751-755, 763 positioned in one or more chambers of the heart 790. The intracardiac electrodes 741, 742, 751-755, 763 may be coupled to impedance drive/sense circuitry 730 positioned within the housing of the pulse generator 705.

In one implementation, impedance drive/sense circuitry 730 generates a current that flows through the tissue between an impedance drive electrode 751 and a can electrode on the housing 701 of the pulse generator 705. The voltage at an impedance sense electrode 752 relative to the can electrode changes as the patient's transthoracic impedance changes. The voltage signal developed between the impedance sense electrode 752 and the can electrode is detected by the impedance sense circuitry 730. Other locations and/or combinations of impedance sense and drive electrodes are also possible.

The lead system 710 may include one or more cardiac pace/sense electrodes 751-755 positioned in, on, or about one or more heart chambers for sensing electrical signals from the patient's heart 790 and/or delivering pacing pulses to the heart 790. The intracardiac sense/pace electrodes 751-755, such as those illustrated in FIG. 5, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The lead system 710 may include one or more leads each having one or more electrodes that extend into the heart. FIG. 5 shows three such leads, one that extends into the right atrium, one that extends into the right ventricle, and one that extends into a coronary vein for placement at the surface of the left ventricle. The left ventricular lead, in particular, includes an LV distal electrode 755 and an LV proximal electrode 754 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 705 may include circuitry for detecting cardiac arrhythmias and/or for controlling pacing or defibrillation therapy in the form of electrical stimulation pulses or shocks delivered to the heart through the lead system 710. The pulse generator 705 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and 6,993,389, which are hereby incorporated herein by reference.

For purposes of illustration, and not of limitation, various embodiments of devices implemented in accordance with the present invention are described herein in the context of PIMDs that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region. (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and, optionally, deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. Patent Publication No. 2004/0230230 and U.S. Pat. No. 7,499,750, which are hereby incorporated herein by reference.

Figure 6:
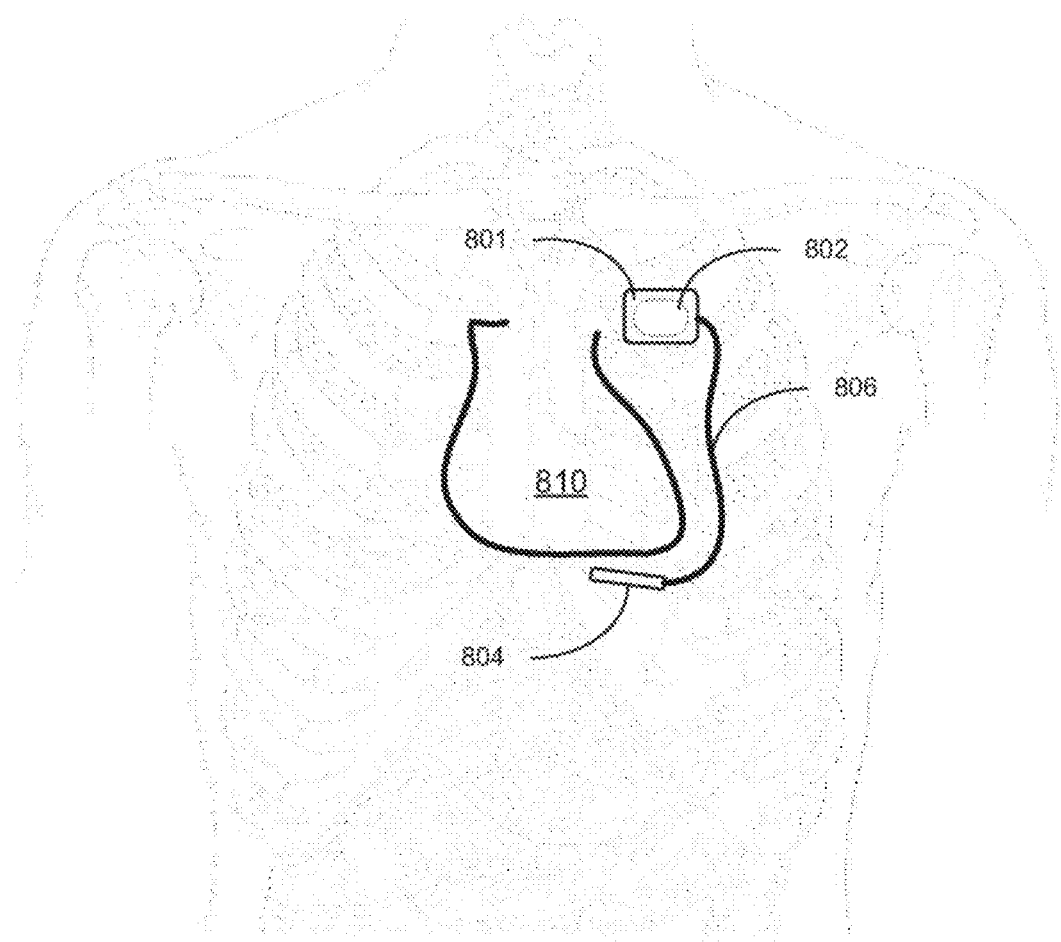
FIG. 6 is an illustration of an implantable medical device including a subcutaneous, non-intrathoracic lead assembly shown implanted outside the ribcage, the implantable medical device implemented to sense one or more physiologic parameters of a patient in accordance with embodiments of the invention.

In one configuration, as is illustrated in FIG. 6, electrode subsystems of a PIMD system are arranged about a patient's heart 810. The PIMD system includes a first electrode subsystem, comprising a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 802 is positioned on the housing 801 that encloses the PIMD electronics. In one embodiment, the can electrode 802 includes the entirety of the external surface of housing 801. In other embodiments, various portions of the housing 801 may be electrically isolated from the can electrode 802 or from tissue. For example, the active area of the can electrode 802 may include all or a portion of either the anterior or posterior surface of the housing 801 to direct current flow in a manner advantageous for cardiac sensing and/or stimulation. For example, portions of the housing 801 may be covered with a non-conductive, or otherwise electrically resistive, material to direct current flow. Suitable non-conductive material coatings include those formed from silicone rubber, polyurethane, or parylene, for example.

The PIMD system shown in FIG. 6 incorporates one or more sensors configured to sense a parameter useful for assessing decongestive therapy and/or a patient's diuresis status. A sensor may be disposed on housing 801, such that element 802 may be representative of such sensor(s) alone or in combination with a can electrode. A sensor(s) may be disposed on another component of the PIMD system, such as on lead 806, a lead separate from lead 806, or on the subsystem element 804, which may be representative of such sensor(s) alone or in combination with a cardiac electrode.

A PIMD of the present invention may be implemented to communicate with a patient management server or network via an appropriate communications interface or an external programmer. A PIMD of the present invention may be used within the structure of an advanced patient management (APM) system. The advanced patient management system allows physicians to remotely and automatically monitor cardiac and respiratory functions, as well as other patient conditions, such as thoracic fluid levels. In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a PIMD or patient-external medical device. It is understood that a wide variety of PIMDs, external medical devices, and other implantable monitoring and/or stimulation device configurations are contemplated, ranging from relatively sophisticated to relatively simple designs. As such, particular medical device configurations may include particular features as described herein, while other such device configurations may exclude particular features described herein.

Various modifications and additions can be made to the preferred embodiments discussed hereinabove without departing from the scope of the present invention. For example, the methods and systems described herein generally include an implantable device or sensor for measuring one or more physiologic parameters of the patient. It is understood that methods and systems of the present invention may be implemented using patient-external devices and sensors, and that the embodiments described herein may be implemented in the context of such patient-external devices and sensors. Moreover, techniques of the present invention may be used in chronic treatment of a patient for general diuretic maintenance as well as acute management of emergent diuretics for congestive event resolution. Accordingly, the scope of the present invention should not be limited by the particular embodiments described above, but should be defined only by the claims set forth below and equivalents thereof.

What is claimed is:

1. A method of operating a medical device system for assessing decongestive therapy delivered to a heart failure patient, comprising:
    sensing a physiologic parameter indicative of the patient's diuresis status via a sensing circuit of the medical device system;
    delivering the sensed physiologic parameter to a processing module of the medical device system;
    determining, by the processing module, when a target level of patient diuresis has been achieved based on either:
    (1) a change of the sensed physiologic parameter that matches a specified value of the physiologic parameter for a previous prior success of achieving the target level of patient diuresis; or
    (2) a rate of change of a difference between the sensed physiologic parameter and a target parameter threshold meeting a target rate of change; and
    producing an output in response to determining that the target level of patient diuresis has been achieved according to the processing module determination, wherein the output comprises one or more of adjusting system-regulated decongestive therapy and presenting a patient response to therapy notification via a user interface of the medical device system.

2. The method of claim 1, further comprising detecting an occurrence of a congestive event, and sensing the physiologic parameter in response to detection of the congestive event.

3. The method of claim 1, wherein the method is performed for chronic diuretic therapy and acute management of emergent diuretic therapy responsive to a congestive event.

4. The method of claim 1, further comprising titrating the decongestive therapy based on the produced output.

5. The method of claim 1, further comprising generating an alert in response to detecting over-diuresis of the patient.

6. The method of claim 1, further comprising generating an alert in response to detecting non-compliance to a drug regimen of the decongestive therapy.

7. The method of claim 1, further comprising generating an alert in response to detecting a threshold degree of refractoriness to the decongestive therapy.

8. The method of claim 1, wherein the method is performed in real-time during delivery of the decongestive therapy.

9. The method of claim 1, further comprising adjusting sensing of the physiologic parameter based on one or more of a type of medication administered to the patient for decongestive therapy, a manner of delivering the decongestive therapy, and one or more patient specific conditions.

10. The method of claim 1, wherein the sensing circuit is included in an implantable device of the medical device system.

11. The method of claim 1, wherein the determining if the target level of patient diuresis has been achieved is performed external to the patient.

12. The method of claim 1, wherein the physiologic parameter comprises at least one of a thoracic fluid parameter, a thoracic impedance parameter, a heart sounds parameter, a cardiac chamber pressure parameter, an arterial pressure parameter, a respiration parameter, heart rate parameter, heart rate variability parameter, an electro gram conduction pattern parameter, a blood chemistry parameter, a potassium level parameter, a blood perfusion parameter, a blood oxygen saturation parameter, a body extremity temperature parameter, a body extremity perspiration parameter, and a patient weight parameter.

13. The method of claim 1, wherein the target parameter threshold is input to the medical device system via the user interface.

14. A method of operating a medical device system for assessing a decongestive therapy delivered to a heart failure patient, comprising:
  sensing a physiologic parameter indicative of the patient's status responsive to the therapy via a sensing circuit of the medical device system;
  delivering the sensed physiologic parameter to a processing module of the medical device system, wherein the processing module is configured to determine a patient's diuresis status;
  the processing module further configured to determine when a target level of therapy benefit to the patient has been achieved based on a rate of change of a difference between the sensed physiologic parameter and a target parameter threshold meeting a target rate of change, wherein the target parameter threshold corresponds to an established safe level of patient diuresis; and
  producing, according to a patient diuresis status determined by the processing module, a first output to indicate that the target level of patient benefit has been achieved and a second output including, in response to determining that the patient is subject to over-therapeuting, one or more of adjusting a system-regulated decongestive therapy and presenting notification of the over-therapeuting via a user interface.

15. The method of claim 14, wherein the therapy comprises a drug therapy.

16. The method of claim 14, wherein the therapy comprises a neurostimulation therapy.

17. The method of claim 14, wherein the therapy comprises a cardiac electrical stimulation therapy.

18. The method of claim 14, wherein the method is performed for chronic diuretic therapy and acute management of emergent diuretic therapy responsive to a congestive event.

19. The method of claim 14, further comprising titrating the therapy based on at least one of the first output and the second output.

20. The method of claim 14, wherein the target parameter threshold is input to the medical device system via the user interface.

* * * * *